United States Patent
Rudolph

(10) Patent No.: US 6,192,886 B1
(45) Date of Patent: *Feb. 27, 2001

(54) NASAL MASK

(75) Inventor: Kevin A. Rudolph, Overland Park, KS (US)

(73) Assignee: Hans Rudolph, Inc., Kansas City, MO (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/734,469

(22) Filed: Oct. 17, 1996

(51) Int. Cl.[7] .................................................. A61M 16/06
(52) U.S. Cl. .............................. 128/207.13; 128/207.18; 128/206.24; 128/207.17; 128/205.25
(58) Field of Search .................... 128/207.13, 204.18, 128/206.24, 206.25, 206.18, 204.12, 207.17, 206.27

(56) References Cited

U.S. PATENT DOCUMENTS

| | | | | |
|---|---|---|---|---|
| H397 | * | 1/1988 | Stark | 128/206.24 |
| D. 322,318 | | 12/1991 | Sullivan . | |
| 628,111 | * | 7/1899 | McHatton | 128/206.18 |
| 1,081,745 | | 12/1913 | Johnston et al. . | |
| 1,288,647 | | 12/1918 | Miller | 128/207.13 |
| 1,837,591 | * | 12/1931 | Shindel | 128/206.34 |
| 2,087,042 | * | 7/1937 | Phillips | 128/206.18 |
| 2,241,535 | * | 5/1941 | Boothby et al. | 128/207.13 |
| 2,477,706 | * | 8/1949 | Taylor | 128/207.13 |
| 2,820,651 | * | 1/1958 | Phillips | 128/204.18 |
| 3,234,939 | * | 2/1966 | Morton, Jr. | 128/206.27 |

(List continued on next page.)

FOREIGN PATENT DOCUMENTS

| | | | | |
|---|---|---|---|---|
| 208855 | * | 5/1940 | (CH) . | |
| 701690 | | 12/1940 | (DE) | 128/207.13 |
| 865111 | * | 1/1953 | (DE) | 128/206.17 |
| 950429 | | 10/1956 | (DE) | 128/207.11 |
| 0549 299 A2 | | 6/1993 | (EP) | 128/207.18 |
| 780746 | | 5/1935 | (FR) | A61M/16/00 |
| 848215 | * | 9/1960 | (GB) | 128/206.24 |
| 276496 | * | 7/1930 | (IT) | 128/206.18 |

OTHER PUBLICATIONS

Page 43 of *Hosptial Accessories Catalog*, 1993–94 showing Sullivan Nasal Bubble Masks and ADAM Nasal CPAP Circuit.

(List continued on next page.)

Primary Examiner—John G. Weiss
Assistant Examiner—V. Srivastava
(74) Attorney, Agent, or Firm—John C. McMahon

(57) ABSTRACT

A nasal mask configured to be as unobtrusive as possible while providing an air-tight seal around the nose of a wearer comprises a flexible nasal cup having a nasal opening formed by an inner circumferential edge or rim thereof and opening into a nasal chamber. The cup also includes inner and outer sealing flanges extending around the rim for forming an air-tight seal during use. The nasal cup is sized such that, when the nasal cup is positioned over a wearer's nose, the rim generally extends across the wearer's upper lip, around the alae of the nose, and across the dorsum of the nose. Opposite ends of a malleable strip are secured to the outer sealing flange and the strip extends across the portion of the outer sealing flange adapted to be positioned over the nasal dorsum. The strip is manually adjustable so that a user may selectively adjust the shape of the mask about the nose to improve the seal across the nose. An airflow passageway extends through the mask at an outer end thereof and is in flow communication with the nasal chamber for delivering air to and removing exhaled air from the nasal chamber. The nasal mask is specifically shaped to provide adequate airflow to the wearer's nose.

1 Claim, 2 Drawing Sheets

U.S. PATENT DOCUMENTS

| | | | | |
|---|---|---|---|---|
| 4,167,185 | * | 9/1979 | Lewis | 128/206.24 |
| 4,328,797 | * | 5/1982 | Rollins, III et al. | 128/206.24 |
| 4,414,973 | * | 11/1983 | Matheson et al. | 128/206.24 |
| 4,655,213 | * | 4/1987 | Rapoport et al. | 128/207.13 |
| 4,657,010 | * | 4/1987 | Wright | 128/206.24 |
| 4,674,492 | | 6/1987 | Niemeyer | 128/202.22 |
| 4,677,977 | * | 7/1987 | Wilcox | 128/206.24 |
| 4,944,310 | | 7/1990 | Sullivan . | |
| 5,074,297 | * | 12/1991 | Venegas | 128/204.18 |
| 5,117,819 | * | 6/1992 | Servidio et al. | 128/204.18 |
| 5,237,986 | * | 8/1993 | Seppala | 128/201.23 |
| 5,243,971 | * | 9/1993 | Sullivan et al. | 128/204.18 |
| 5,265,595 | | 11/1993 | Rudolph | 128/204.18 |
| 5,522,382 | | 6/1996 | Sullivan et al. | 128/204.23 |
| 5,549,103 | * | 8/1996 | Johnson | 128/207.18 |
| 5,558,089 | * | 9/1996 | Castiglione | 128/206.24 |
| 5,611,334 | * | 3/1997 | Muchin | 128/207.18 |
| 5,617,849 | * | 4/1997 | Springett et al. | 128/206.24 |
| 5,724,965 | * | 3/1998 | Handke et al. | 128/207.18 |
| 5,738,094 | * | 4/1998 | Hoftman | 128/206.24 |

OTHER PUBLICATIONS

Photographs of a nasal mask produced by Hans Rudolph, Inc., units of which were sold more than one year prior to the filing date of the above–captioned application.

Copy of packaging of All–Seasons Dust Mask of Ace Harware Corporation, sold more than one year prior to the filing date of the above–captioned application.

* cited by examiner

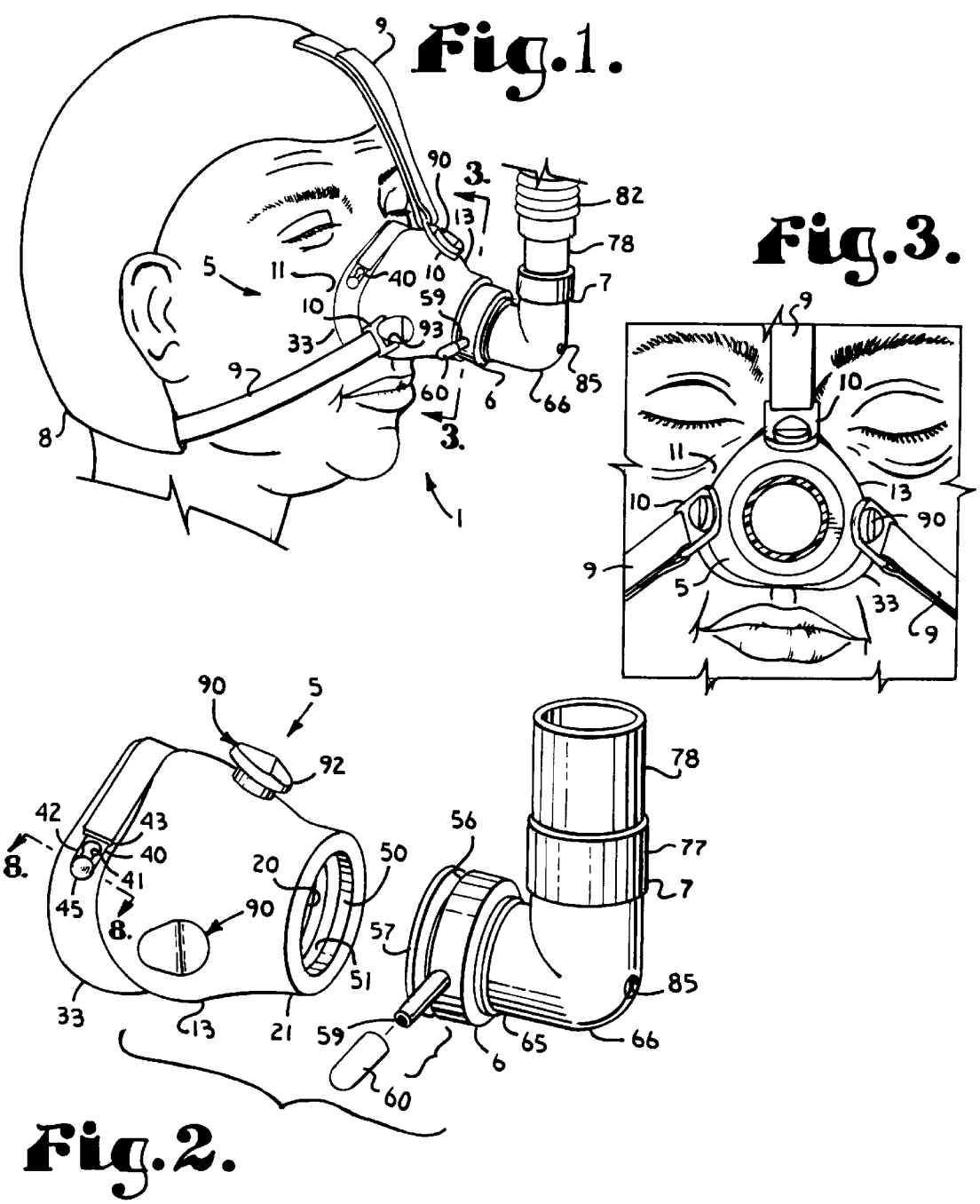

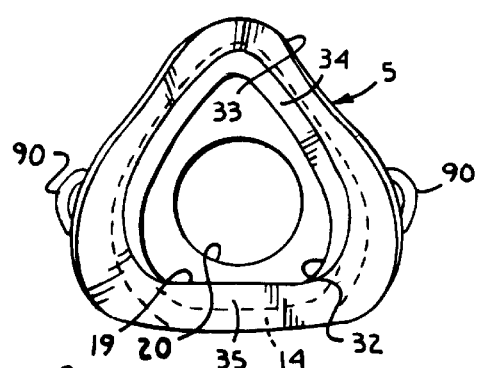
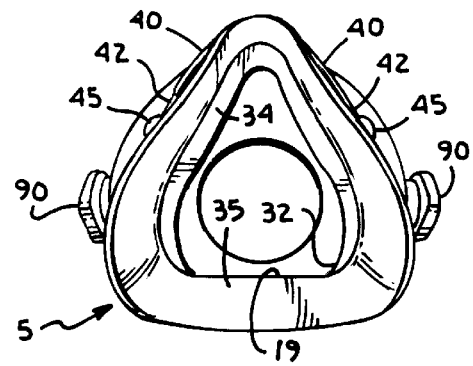
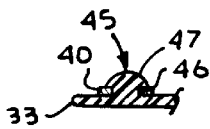
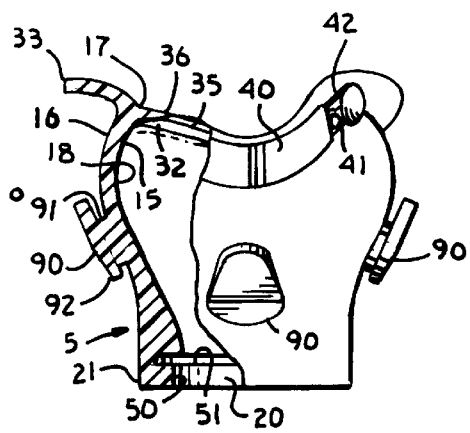

NASAL MASK

BACKGROUND OF THE INVENTION

The present invention relates to an improved nasal mask for delivering positive air pressure to the nasal passages to facilitate treatment of breathing disorders such as sleep apnea, ventilation difficulties or anesthetic gas administration.

Obstructive sleep apnea is caused by obstruction of the upper airway during sleep which results in the absence of airflow through the nose or mouth for at least 10 seconds. Obstructive sleep apnea episodes are usually most severe during periods of REM (Rapid Eye Movement) sleep, when muscle tone is inhibited. The upper airway then narrows as a result of the relaxation of a number of muscles. The suction pressure of inspiration then causes further narrowing or collapse of the airway. The lack of airflow causes the oxygen level in the blood to drop causing arousal which then restores upper airway muscle tone allowing normal breathing.

Heavy snoring and daytime sleepiness are the most common symptoms associated with obstructive sleep apnea syndrome. Other complaints include night-time thrashing, sleep walking, enuresis, disorientation, personality changes, intellectual deterioration, sexual dysfunction, hypnagogic hallucinations, automatic behavior and morning headaches. The prevalence of episodes of obstructive apnea and the frequency of occurrence increase with age. Men are much more commonly affected than women and nearly 50% of elderly men have 20 or more apneic episodes each night. Other known risk factors include obesity, chronic alcoholism, chronic obstructive pulmonary disease and post-menopausal state. Altogether more than 30,000 patients are treated each year for obstructive sleep apnea.

The most effective and frequent therapy for obstructive sleep apnea is application of continuous positive airway pressure (CPAP). For such therapy, a patient is fitted with a tight fitting nasal mask connected through an airway to a blower which supplies air at a slight positive pressure to the nasal passages. The application of the slight positive pressure is immediately effective in reversing airway obstruction in most patients with obstructive sleep apnea. Although the therapeutic results of nasal CPAP are often dramatic and immediate, it is only effective when used properly and on a regular basis. Failure to apply nasal CPAP for even a single night results in recurrence of hypersomnolence the next day.

Problems associated with wearing existing masks or positive airway pressure delivery systems during periods of attempted sleep are sufficient to deter many patients from continuing CPAP therapy. Some problems include excessive noise and irritation resulting from leaks around improperly fitting masks or general discomfort caused by the design of the mask or the CPAP delivery system. Leakage of air between the mask and the face often allows air to blow on the eyes which wakes the patient and/or substantially irritates the eyes.

SUMMARY OF THE INVENTION

The present invention comprises a nasal mask configured to be as unobtrusive as possible while providing an air-tight seal around the nose of a wearer. The mask comprises a flexible nasal cup having a nasal opening extending across an inner circumferential edge thereof and having a nasal chamber formed therein. The nasal cup is sized for insertion over a portion of the wearer's nose (preferably almost the entire nose), such that the inner circumferential edge of the cup generally extends across the upper lip, around the alae of the nose, and across the dorsum of the nose.

The nasal mask includes an inner and an outer sealing flange extend inward and outward respectively from the inner circumferential edge of the nasal cup. The sealing flanges cooperate to provide an improved seal. An airflow passageway extends through the mask at an outer end thereof and in communication with the nasal chamber for delivering air to and removing exhaled air from the nasal chamber. The nasal mask is specifically shaped to provide adequate air-flow to the wearer's nose.

The nasal mask includes a malleable pliable strip secured to the outer sealing flange so as to extend up and over the portion of the mask extending over the rear of the wearer's nose. The pliable strip may be bent or shaped to modify the shape of the mask to adjust the fit of the mask and improve the seal of the mask across the nose.

OBJECTS AND ADVANTAGES OF THE INVENTION

The objects of the present invention include providing a nasal mask which is as unobtrusive as possible while providing an air-tight seal; to provide such a mask which provides adequate air-flow around the wearer's nose; to provide such a mask which may be firmly secured to a wearer's face; to provide such a mask having means for adjusting the fit of the mask across the nose of a wearer's face; to provide such a mask comprising a nasal cup into which the nose of a wearer may be inserted such that an inner circumferential edge of the nasal cup extends across the upper lip below the wearer's nose, around the alae of the nose and across the dorsum of the nose; to provide such a mask having inner and outer sealing flanges extending inward and outward from the inner circumferential edge of the nasal cup respectively for providing a seal; to provide such a mask in which the outer sealing flange does not extend across portions of the eye sockets; to provide such a mask in which an upper edge of the mask engages the nose below the root of the nose; to provide such a mask in which the nasal cup is formed from flexible material; to provide such a mask in which the nasal cup is adapted to be secured to tubing for supplying gas under pressure to the interior of the mask; to provide such a mask in which the tubing is swivelably connected to the nasal cup; to provide such a mask which is relatively easy to assemble; to provide such a mask which is relatively easy to put on by a wearer; to provide such a mask which is relatively inexpensive to manufacture and which is particularly well adapted for its intended purpose.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a perspective view of the nasal mask assembly, including a nasal mask, in accordance with the present invention secured to a wearer over the wearer's nose.

FIG. 2 is an enlarged and exploded perspective view of the nasal mask and associated airflow tubing assembly.

FIG. 3 is a fragmentary front elevational view of the mask secured to the face of a wearer, as shown in FIG. 1, with portions of the airflow tubing assembly broken away to show detail.

FIG. 4 is an enlarged rear elevational view of the nasal mask with a malleable positioning strip thereof in an initial non compressed state.

FIG. 5 is an enlarged rear elevational view of the nasal mask with the positioning strip in a partially compressed state.

FIG. 6 is an enlarged top plan view of the nasal mask with portions broken away to show detail thereof.

FIG. 7 is an enlarged and fragmentary cross-sectional view of the nasal mask positioned on a patient, taken generally along line 7—7 of FIG. 1.

FIG. 8 is an enlarged and fragmentary cross-sectional view of the nasal mask showing a connector, taken along line 8—8 of FIG. 2.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail, the reference numeral 1 refers to a nasal mask assembly of the present invention. The nasal mask assembly 1 includes a nasal mask 5, an annular swivel connector 6, an airflow tubing assembly 7, a flexible cap 8, adjustable straps 9 and strap fasteners 10. The nasal mask 5 is shown secured to the face 11 of a user in FIG. 1. Directional references herein will generally be with reference to the nasal mask 5 as oriented in FIG. 7 with the front and rear of the mask 5 being to the right and left of the sheet respectively and the top and bottom of the mask 5 being to the top and bottom of the sheet respectively. Other directional references are generally based on the same orientation.

The nasal mask 5 is preferably constructed of silicone or other like material that is flexible and resilient and which does not cause substantial skin irritation to the wearer. The nasal mask 5 includes a cup-like structure, or nasal cup 13 generally formed from a continuous wall 14 having an inner surface 15, an outer surface 16 and a rim or first end 17. The continuous wall generally defines a nasal cavity or chamber 18 therein.

A nasal opening 19 generally extends across the rim 17 of the nasal cup 13 and opens into the nasal chamber 18. A connector receiving opening 20, adapted to receive the swivel connector 6 for securement thereto, is formed in the nasal cup 13 at front end 21 thereof opposite the rim 17. The nasal cup 13 is sized for placement over a wearer's nose 25 such that the nose 25 extends through the nasal opening 19 and into the nasal chamber 18. The rim 17 generally extends across the wearer's upper lip 26, around the alae 27 of the nose and across the nasal dorsum 28, below the root 29 thereof.

An inner sealing flange 32 extends inward from the rim 17 of the nasal cup 13 generally transverse thereto so as to engage a wearer's face 11 when the nasal cup 13 is positioned thereagainst. The inner sealing flange 32 preferably extends completely around the rim 17. The inner sealing flange 32 is generally an extension of and comprises a thin layer of the flexible and resilient material used to construct the rest of the nasal cup 13.

The nasal cup 13 also includes an outer sealing flange 33 which extends outward from the rim 17 so as to engage a wearer's face 11 when the nasal cup 13 is positioned thereagainst. The outer sealing flange 33 preferably extends around the sides and across the top of the nasal cup 13, but not around the bottom of the nasal cup 13. The outer sealing flange 33 is generally wider proximate the alae 27 of the nose 25 and narrower across the portion extending adjacent the eye sockets of the wearer such that the outer sealing flange 33 generally does not extend across portions of the eye socket which would result in user discomfort. The outer sealing flange 33 is generally an extension of and comprises a thin layer of the flexible and resilient material used to construct the rest of the nasal cup 13.

The inner sealing flange 32 generally comprises two portions, an upper portion 34 and a lower portion 35. The upper portion 34 generally extends along the sides of the nasal cup 13 and across the upper periphery thereof so as to generally engage the wearer's face 11 along the sides of the nose 25, over the nasal dorsum 28 and around, but not below the alae 27. The lower portion 35 generally extends across the bottom of the nasal cup 13 so as to generally engage the face 11 above the upper lip 26 of the wearer and to extend below the alae 27. Although it is preferable that the upper portion 34 and the lower portion 35 of the inner sealing flange 32 are generally contiguous, it is foreseen that a gap could extend between the upper portion 34 and the lower portion 35 generally around the alae 27 of the nose such that the inner sealing flange 32 only substantially completely extends around the rim 17. It is further foreseeable that other slight breaks in the inner sealing flange 32 could be incorporated into the mask 5.

The upper portion 34 of the inner sealing flange 32 is also formed to be thinner than the lower portion 35 and thinner than the outer sealing flange 33. The lower portion 35 of the inner sealing flange 32 is preferably approximately the same thickness as the outer sealing flange 33.

The nasal cup 13 may be generally described as having a bulbous nose shape. The continuous wall 14 of the nasal cup 13 generally curves outward and then back inward from the rim 17 along the sides and across the top of the cup 13 so as to generally bulge out around the alae 27 and across the bridge or dorsum 28 of the nose 25. The continuous wall 14 then converges toward the front end 21 of the nasal cup 13. The vertical cross-section of the of the nasal cup 13 may also be described as a rounded triangle (that is, generally triangular in shape with rounded corners). The nasal opening 19, whose outer edge is generally defined by the inner sealing flange 32, may also be generally described as a rounded triangle in shape. The bulbous shape of the nasal mask 5 that generally spaces the mask 5 from the nose 25 is to provide space for air flow around the nose 25 to facilitate breathing.

The shape of the nasal mask 5 generally along the rim 17 is adjustable by a strip 40 of pliable material secured thereto. The pliable strip 40 is preferably formed from a malleable metal such as aluminum alloy 3003 H14 or the like and includes mounting apertures 41 at opposite ends 42 thereof. The pliable strip 40 of aluminum alloy includes a sheath or cover 43 covering a substantial portion of the pliable strip 40. Shrink tape is a preferred material for use as the sheath 43. The sheath 43 covers burrs and the like on the strip 40 and improves the aesthetics of the strip 40 which is generally formed by punching from a sheet of metal. Two strip mounting buttons 45, each having a shaft 46 and an enlarged head 47 are integrally formed on the outer sealing flange 33 on opposite sides thereof and positioned to generally be placed proximate the base of the nose 25 when the nasal cup 13 is placed over the nose 25. The strip mounting buttons 45 are preferably formed from the same flexible and resilient material as the nasal cup 13. The strip 40 is secured to the nasal mask 5 by pressing the enlarged head 47 of the buttons 45 through the apertures 41 in the opposite ends 42 of the strip 40. The strip 40 then preferably extends up and over the interface between the nasal cup 13 and the outer sealing flange 33 on the portion of the nasal mask 5 adapted to be positioned over the nasal dorsum 28.

FIG. 4 shows a rear view of the nasal mask 5 in a generally normal state wherein the shape of the nasal mask 5 is in a relaxed state prior to modification by the pliable strip 40. FIG. 5 shows a rear view of the nasal mask 5 in which the ends 42 of the pliable strip 40 have been pressed toward each other relative to their positional relationship shown in FIG. 4, so as to modify the shape of the nasal mask 5 into one of an infinite number of modified states. The shape of the nasal mask 5 in FIG. 5 has been modified such that the nasal opening 19 has been narrowed to provide a snugger fit for a particular nose and each of the various modified states available fits different nose shapes.

The front end 21 of the nasal cup 13 is generally cylindrical with the connector receiving opening or airflow passageway 20 extending therethrough in communication with the nasal chamber 18. The opening 20 is generally positioned toward the bottom of the nasal cup 13 so as to be generally in front of the naries 38 of the nose 25.

The connector receiving opening 20 is defined by a grooved circular shoulder 50 extending through the wall 14 at a front end thereof. A flange receiving groove 51 extends into the wall 14 along and parallel to the grooved circular shoulder 50.

The airflow tubing assembly 7 is connected to the nasal mask 5 at the connector receiving opening 20 by the annular swivel connector 6 formed from a relatively rigid plastic and having an airflow passageway 55 extending therethrough. A shoulder receiving groove 56 is formed on an outer surface of the annular swivel connector 6 toward a rear end thereof so as to form an annular connecting flange 57 on the rear end of the annular swivel connector 6. The annular swivel connector 6 is snugly securable to the nasal mask 5 by insertion of the connecting flange 57 into the flange receiving groove 51 of the nasal mask 5 such that the front portion of the grooved circular shoulder 50 extends into the shoulder receiving groove 56 and seals thereabout. The frictional engagement of the flange 57 by the nasal mask 5 resists rotation of the annular swivel connector 6 relative thereto.

Two sampling ports 59 with caps 60 are formed on opposite sides of the connector 6 and flow communicate with the airflow passageway 55 extending therethrough. The airflow passageway 55 flow communicates with the nasal chamber 18 through the nasal opening 19.

An annular ridge 62 is formed on and extends radially inward from an inner surface of the annular swivel connector 6 at a front end thereof. The annular ridge 62 is sized to engage a ridge receiving groove 64 formed in a first end 65 of an elbow 66 having an airflow passageway 67 extending therethrough. The first end 65 of the elbow 66 includes a beveled leading ridge 68 to allow the first end 65 of the elbow 66 to generally be snapped into the annular swivel connector 6 with the annular ridge 62 on the connector 6 engaging the groove 64 in the first end 65 of the elbow 66. The elbow 66 freely rotates or swivels relative to the annular swivel connector 6.

A second end 70 of the elbow 66 includes a beveled ridge 71 and a ridge receiving groove 72 sized for insertion into a first end 77 of a tube 78 having an airflow passageway 79 extending therethrough and in inwardly directed annular ridge 80 at the first end 77 thereof. The annular ridge 80 engages the ridge receiving groove 72 when the second end 70 of the elbow 66 is inserted in the first end 77 of the tube 78 for securing the tube 78 to the elbow 66 and to permit the tube 78 to swivel relative to the second end 70 of the elbow 66. A flexible tube 82 is connected to a second end 83 of the tube 78. The flexible tube 82 is connected to apparatus for providing pressurized air to the wearer of the nasal mask assembly 1 through the annular swivel connector 6 and the airflow tubing assembly 7 which generally comprises the flexible tube 82, the tube 78 and the elbow 66.

An exhalation discharge aperture, opening or port 85 is formed in the elbow 66 preferably in line with the airflow passageway 55 through the annular swivel connector 6. The exhalation discharge port 85 is sized to allow exhaled air to escape yet small enough to maintain adequate pressure to provide sufficient continuous positive airway pressure to treat sleep apnea.

Three strap securement buttons 90 are integrally formed on the outer surface 15 of the nasal cup 13 for securement of the strap fasteners 10 thereto. The buttons 90 are adapted to removably receive the strap fasteners 10 which cooperate with the adjustable securement straps 9 and the cap 8 to secure the nasal mask 5 in place against the face 11 of a user.

The buttons 90 are integrally formed of the same flexible material as the rest of the mask 5 and comprise a post 91 and a circumferential flange or enlarged head 92. The post 91 extends perpendicularly away from the outer surface 15 of the mask 5 and is generally cylindrical. The strap fasteners 10 include a button receiving aperture 93 and a strap receiving slot 94. The strap fasteners 10 are secured to a respective button 90 by pressing the flexible button 90 through a respective button receiving aperture 93 in the fastener 10. The strap fastener 10 is then rotatable about the post 91. A free end of the adjustable strap 9 is threaded through the strap receiving slot 94 and secured back on to itself by adjustable fastening means such as a hook and loop type fastener.

Two of the buttons 90 are positioned on opposite sides of the nasal cup 13 generally on the portion of the cup 13 covering the alae 27. The third button 90 is positioned along the upper periphery of the nasal cup 13. The buttons 90 are positioned on an outwardly sloping portion of the outer surface 15 of the cup 13 when looking at the cup 13 on a user's face 11 as in the orientation of FIG. 3.

It is to be understood that while certain forms of the present invention have been illustrated and described herein, it is not to be limited to the specific forms or arrangement of parts described and shown.

What is claimed is:

1. A nasal mask assembly including:
   a) a nasal mask comprising:
      i) a flexible nasal cup having a nasal opening formed along a rim thereof, a first airflow passageway extending through said cup generally opposite said nasal cup and a nasal chamber formed therein; said nasal cup sized and adapted for placement over the wearer's nose such that said rim generally extends across the wearer's upper lip, around both alae of the nose, and across the dorsum of the nose;
      ii) an inner sealing flange extending inward from said nasal cup rim substantially completely therearound; and iii) an outer sealing flange extending outward from said nasal cup rim along a portion of said rim extending around the alae of the nose, and across the dorsum of the nose and being discontinuous along a portion of said rim extending across the wearer's upper lip; at least upper portions of said inner sealing flange extending along opposite sides of said nasal cup and adapted to engage a wearer's face along the sides of the nose being thinner than said outer sealing flange;

iv) a lower portion of said inner sealing flange which is adapted to be positioned to extend across an upper lip of a wearer is approximately the same thickness as the outer sealing flange;

b) first and second strap securement buttons integrally formed on an outer surface of said mask on opposite sides thereof;

c) a third strap securement button integrally formed on said outer surface of said mask on an upper surface thereof on a portion of the nasal mask extending across the dorsum of the nose; and d) first, second and third straps removably securable at first ends thereof to said first, second and third strap securement buttons for securing said nasal mask to the head of a wearer;

e) a malleable strip formed from metal and having a sheath covering a substantial portion thereof is secured to said nasal mask proximate said nasal opening so as to extend across a portion of the nasal mask extending across the dorsum of the nose whereby the shape of said strip can be manually modified to in turn modify the shape of the nasal mask and the fit of the cup at the nasal opening;

f) a pair of strip mounting buttons each comprising a shaft and an enlarged head are integrally formed on said nasal mask on opposite sides thereof;

g) each end of said strip includes an aperture that is sized for pressing said head of a respective strip mounting button therethrough for securing said strip thereto;

h) an annular connector having a second airflow passageway extending therethrough and removably securable to said nasal mask in flow communication with said first airflow passageway; and i) a tubing assembly swively connected to said annular connector.

* * * * *